US008989343B2

(12) United States Patent
Arai et al.

(10) Patent No.: US 8,989,343 B2
(45) Date of Patent: Mar. 24, 2015

(54) IMAGE PROCESSING DEVICE, X-RAY CT PHOTOGRAPHIC APPARATUS, AND IMAGE PROCESSING METHOD

(71) Applicants: Nihon University, Chiyoda-ku, Tokyo (JP); J. Morita Manufacturing Corporation, Kyoto-shi, Kyoto (JP)

(72) Inventors: Yoshinori Arai, Chiyoda-ku (JP); Masakazu Suzuki, Kyoto (JP)

(73) Assignees: Nihon University, Tokyo (JP); J. Morita Manufacturing Corporation, Kyoto (JP)

( * ) Notice: Subject to any disclaimer, the term of this patent is extended or adjusted under 35 U.S.C. 154(b) by 153 days.

(21) Appl. No.: 13/871,791

(22) Filed: Apr. 26, 2013

(65) Prior Publication Data
US 2013/0287166 A1 Oct. 31, 2013

(30) Foreign Application Priority Data

Apr. 27, 2012 (JP) ................................ 2012-102804
Apr. 23, 2013 (JP) ................................ 2013-089946

(51) Int. Cl.
*G01N 23/00* (2006.01)
*G06T 7/00* (2006.01)
*G06T 11/00* (2006.01)

(52) U.S. Cl.
CPC ............ *G06T 7/0012* (2013.01); *G06T 11/008* (2013.01)
USPC ............................................... 378/20; 378/4

(58) Field of Classification Search
USPC ...................... 378/4, 15, 20, 22, 901; 382/131
See application file for complete search history.

(56) References Cited

U.S. PATENT DOCUMENTS

| 5,243,664 A | 9/1993 | Tuy |
| 6,125,193 A | 9/2000 | Han |
| 6,721,387 B1 | 4/2004 | Naidu et al. |
| 7,103,135 B2 * | 9/2006 | Koppe et al. ...................... 378/4 |
| 2007/0019780 A1 * | 1/2007 | Haras et al. ...................... 378/4 |
| 2010/0054569 A1 * | 3/2010 | Bruder et al. ................. 382/131 |

FOREIGN PATENT DOCUMENTS

| JP | 2010-99114 A | 5/2010 |
| WO | WO 2005/076221 A | 8/2005 |

OTHER PUBLICATIONS

"Metal artifact reduction in CT using tissue-class modeling and ... " written by Matthieu Bal, et al. in the Medical Physics, vol. 33, No. 8, Jul. 24, 2006, pp. 2852-2859.

* cited by examiner

*Primary Examiner* — Irakli Kiknadze
(74) *Attorney, Agent, or Firm* — DLA Piper LLP (US)

(57) ABSTRACT

An image processing device acquiring pseudo projection data by calculation when a virtual metallic body having a predetermined X-ray absorption coefficient is set in a photographic region of X-ray CT photography in a pseudo manner based on projection data, and the image processing device reconstructing the pseudo projection data to acquire pseudo CT image data. The image processing device acquires luminance (virtual metallic body luminance) of a virtual metallic body in the pseudo CT image data, and specifies a position of a metal equivalent region having luminance corresponding to the virtual metallic body luminance in normal CT image data. The image processing device acquires correction projection data by performing correction processing to the luminance of the metal equivalent region in the normal projection data, and the image processing device reconstructs the correction projection data to acquire correction CT image data.

15 Claims, 10 Drawing Sheets

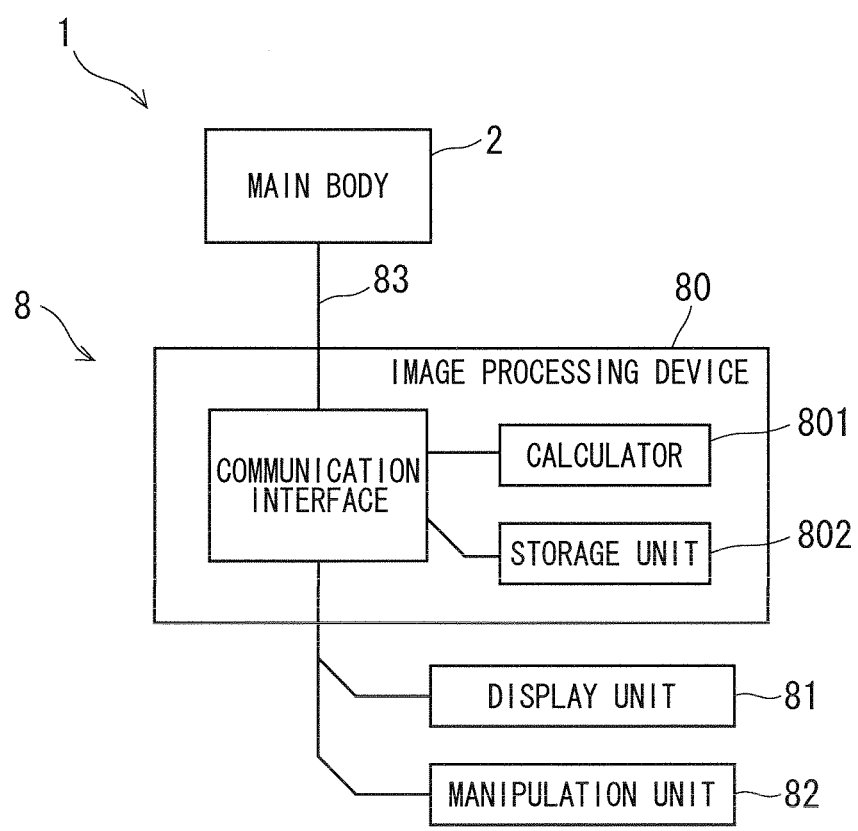
F I G . 2

F I G . 7
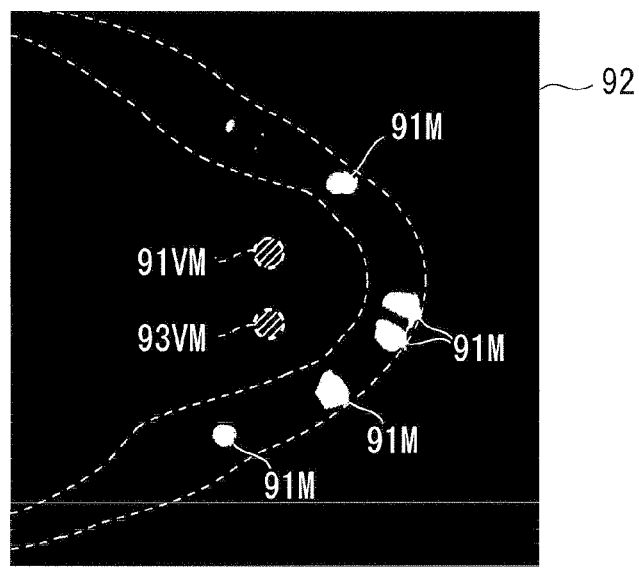
F I G . 8
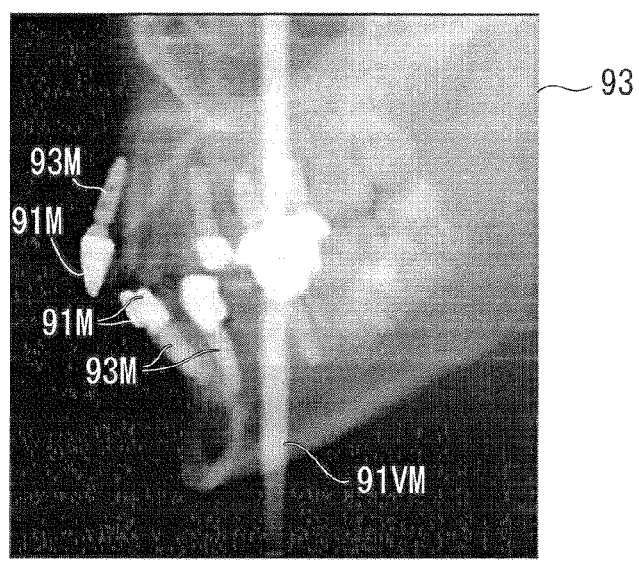

F I G . 1 1
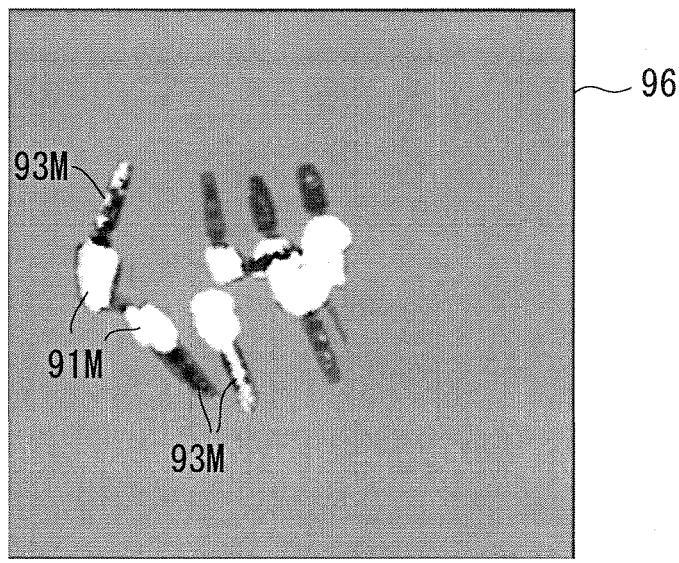
F I G . 1 2
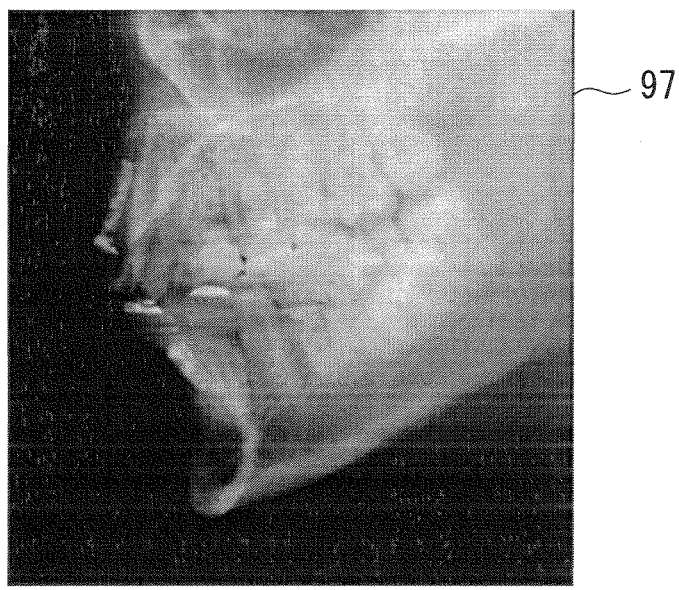

IMAGE PROCESSING DEVICE, X-RAY CT PHOTOGRAPHIC APPARATUS, AND IMAGE PROCESSING METHOD

BACKGROUND OF THE INVENTION

1. Field of the Invention

The present invention relates to a technology of reducing a metallic artifact by extracting a position of a metallic body included in a CT photographic region in X-ray CT photography.

2. Description of the Background Art

Conventionally, the X-ray CT photography is performed in a medical field and the like. In the X-ray CT photography, a subject is irradiated with an X-ray to collect its projection data expressing a projection image, and the projection data is reconstructed on a computer to generate a CT (Computed (Computerized) Tomography) image (tomographic image).

In the X-ray CT photography, the subject is disposed between an X-ray generator and an X-ray detector, the X-ray generator and the X-ray detector turn about the subject, and the X-ray generator emits the conical X-ray (an X-ray cone beam) to the subject. The X-ray detector collects detection result (projection data) of the X-ray, and CT image data (volume data) is reconstructed based on the collected detection result of the X-ray.

In the case that a metallic body having a high X-ray absorption factor is included in the CT photographic region, the X-ray is hardly transmitted through the metallic body, and a correct transmission amount is hardly measured. Therefore, sometimes many streak noises (metallic artifacts) are generated around the metallic body on the CT image (the tomographic image) that is obtained by reconstructing the projection data. In the case that the metallic artifact is generated, a correct image diagnosis is hardly performed. Therefore, some methods of removing the metallic artifact have been proposed (for example, see Japanese Patent Publication Laid-Open No. 2010-099114).

Specifically, in the technology disclosed in Japanese Patent Publication Laid-Open No. 2010-099114, a metal position is specified by binarizing a sinogram generated from the projection data using a predetermined threshold.

However, in this technology, it is necessary to properly set the threshold in order to separate a metallic portion from a non-metallic portion. Therefore, in the case that the threshold is improperly set, possibly the metallic artifact cannot properly be removed because the metal position is hardly specified with high accuracy.

SUMMARY OF THE INVENTION

The present invention is directed to an image processing device that acquires CT image data by reconstructing projection data, which is acquired by performing X-ray CT photography of a region including a metallic body in a subject.

According to the present invention, the image processing device includes: a pseudo projection data acquisition unit that acquires pseudo projection data by calculation when a virtual metallic body having a predetermined X-ray absorption coefficient is set in a photographic region of X-ray CT photography in a pseudo manner based on the projection data; a pseudo CT image data generator that reconstructs the pseudo projection data to generate pseudo CT image data; a virtual metallic body luminance acquisition unit that acquires virtual metallic body luminance that is luminance corresponding to the virtual metallic body in the pseudo CT image data; a position specification unit that specifies a position of a metal equivalent region having luminance corresponding to the virtual metallic body luminance in CT image data, the projection data being reconstructed in the CT image data; a correction processor that acquires correction projection data by performing correction processing to the luminance of the metal equivalent region in the projection data, degradation of X-ray intensity due to X-ray absorption being corrected through the correction processing; and a correction CT image data acquisition unit that reconstructs the correction projection data to acquire correction CT image data.

The luminance of the virtual metallic body arranged in the pseudo manner is acquired to specify the position of the luminance equivalent to the luminance of the virtual metallic body, whereby the position of the metallic body within the photographic region can be specified with high accuracy. Accordingly, the metallic artifact, which is generated in the CT image acquired by the reconstruction, can successfully be reduced by performing the correction processing to the position of the metallic body.

Preferably, the correction processor performs the correction processing to the luminance of the metal equivalent region in the projection data according to the luminance in a surrounding area of the metal equivalent region.

The luminance of the metal equivalent region in which the position is specified is interpolated according to the luminance of the surrounding area. Therefore, the metal equivalent region can be corrected according to the luminance of the surrounding area and as a result, the metallic artifact, which is generated in the CT image (the tomographic image) acquired by the reconstruction, can be reduced.

Preferably, the image processing device further includes a synthesis processor that synthesizes the correction CT image data and the CT image data by converting the luminance of the metal equivalent region in the correction CT image data according to the luminance in an identical position in the CT image data.

The corrected luminance of the metallic portion in the correction CT image data is converted into the luminance in the original CT image data. Therefore, the actual metallic body can be photographed on the CT image in which the metallic artifact is reduced.

Preferably, the projection data is acquired by local X-ray CT photography in which only a partial region in the subject is irradiated with an X-ray.

For the local CT photographic target region, the position of the metallic body in the CT image data can be successfully extracted.

Preferably, the projection data is acquired by an X-ray CT photographic apparatus, and this X-ray CT photographic apparatus includes: an X-ray generator that generates X-ray; an X-ray detector that detects the X-ray transmitted through the subject; a support body that supports the X-ray generator and the X-ray detector while the X-ray generator and the X-ray detector are opposed to each other in relation to the subject; and a support body turning drive unit that turns the support body about a turning shaft to turn the X-ray generator and the X-ray detector about the subject, and the virtual metallic body is formed into a cylinder solid or a substantial cylinder solid so as to extend in parallel with the turning shaft.

The shape of the virtual metallic body arranged in the pseudo manner is formed into the substantial cylinder solid that extends in parallel with the turning shaft of the support body of the X-ray CT photographic apparatus. Therefore, the X-ray absorption degree of the virtual metallic body is substantially homogenized among plural pseudo projection images expressed by the pseudo projection data. Therefore, because the appropriate virtual metallic body luminance can be acquired, the position of the metallic body corresponding to the virtual metallic body can be successfully specified.

Preferably, the X-ray CT photographic apparatus further includes a subject retention unit that retains the subject, and the virtual metallic body is arranged in a pseudo manner in a position different from the metallic body, which is determined based on positional information on the subject, the positional information on the subject being retained in the subject retention unit.

The position of the metallic body existing currently in the subject is specified based on the positional information on the subject, which is retained in the subject retention unit, so that the virtual metallic body can be arranged in the pseudo manner by selecting the position different from the position of the metallic body.

Preferably, the position specification unit distinguishes a metal equivalent region that is equivalent to the virtual metallic body from a region that is not equivalent to the virtual metallic body by binarizing the CT image data with luminance corresponding to the luminance of the virtual metallic body as a threshold.

The region that is equivalent to the metallic body and the region that is not equivalent to the metallic body can be distinguished from each other.

Preferably, the pseudo projection data acquisition unit acquires the pseudo projection data by calculation when the plural kinds of virtual metallic bodies having the X-ray absorption coefficients different from each other are arranged in a pseudo manner based on the projection data, and the position specification unit individually specifies a the position of a region having luminance corresponding to the virtual metallic body luminance of each of the plural kinds of virtual metallic bodies in the CT image data, in which the projection data is reconstructed, as the metal equivalent region.

In the case that the plural kinds of metallic bodies are included in the photographic region of the subject, the position can be specified in each metallic body.

Preferably, the correction processor corrects the luminance by subtracting an X-ray absorption degree of the metal equivalent region corresponding to the virtual metallic body from X-ray absorption degrees of the metal equivalent regions equivalent to some virtual metallic bodies having the low X-ray absorption coefficients in the plural kinds of virtual metallic bodies in the projection data.

The correction projection data, in which the metallic bodies equivalent to some virtual metallic bodies having the high X-ray absorption coefficient are removed from the original projection data, can be generated through the correction processing. Therefore, the CT image can be generated while the information on the X-ray absorption degree in portion except the metallic body is left as much as possible.

Preferably, the position specification unit distinguishes a metallic body region corresponding to the high X-ray absorption coefficient in the two kinds of the virtual metallic bodies, a metallic body region corresponding to the low X-ray absorption coefficient, and a region not corresponding to the two kinds of virtual metallic bodies from one another by quantifying the CT image data to three levels with luminance corresponding to the luminance of each of the two kinds of virtual metallic bodies as a threshold.

The region corresponding to each of the two kinds of metallic bodies and the region except the metallic bodies can be successfully distinguished from each other.

Preferably, the correction processor sets a region where a region of the metallic body position in the projection data is enlarged so as to include at least one adjacent pixel to a target region of the correction processing.

The interpolation processing of the luminance of the metal equivalent region can be reduced based on the luminance that includes the noise generated in the surrounding area of the metallic body on the projection image.

Preferably, the correction processor performs low-pass filter processing to projection data in a boundary portion between the metal equivalent region and a region except the metal equivalent region in the projection data.

Through the low-pass filter processing, the boundary portion between the metallic region and the non-metallic region can be prevented from becoming clear. Therefore, when calculating CT reconstruction, aliasing can be prevented to improve the accuracy of the image reconstruction.

The present invention is also directed to an X-ray CT photographic apparatus that acquires CT image data by reconstructing projection data, which is acquired by performing X-ray CT photography of a region including a metallic body in a subject.

According to the present invention, the X-ray CT photographic apparatus includes: a pseudo projection data acquisition unit that acquires pseudo projection data by calculation when a virtual metallic body having a predetermined X-ray absorption coefficient is set in a photographic region of X-ray CT photography in a pseudo manner based on the projection data; a pseudo CT image data generator that reconstructs the pseudo projection data to generate pseudo CT image data; a virtual metallic body luminance acquisition unit that acquires virtual metallic body luminance that is luminance corresponding to the virtual metallic body in the pseudo CT image data; a position specification unit that specifies a position of a metal equivalent region having luminance corresponding to the virtual metallic body luminance in CT image data, the projection data being reconstructed in the CT image data; a correction processor that acquires correction projection data by performing correction processing to the luminance of the metal equivalent region in the projection data, degradation of X-ray intensity due to X-ray absorption being corrected through the correction processing; and a correction CT image data acquisition unit that reconstructs the correction projection data to acquire correction CT image data.

The present invention is also directed to an image processing method of acquiring CT image data by reconstructing projection data, which is acquired by performing X-ray CT photography of a region including a metallic body in a subject.

According to the present invention, the image processing method includes the steps of: (a) acquiring pseudo projection data by calculation when a virtual metallic body having a predetermined X-ray absorption coefficient is set in a photographic region of the X-ray CT photography in a pseudo manner based on the projection data; (b) reconstructing the pseudo projection data to generate pseudo CT image data; (c) acquiring virtual metallic body luminance of the virtual metallic body in the pseudo CT image data; (d) specifying a position of a metal equivalent region having luminance corresponding to the virtual metallic body luminance in CT image data in which the projection data is reconstructed; (e) acquiring correction projection data by performing correction processing to the luminance of the metal equivalent region in the projection data, degradation of X-ray intensity due to X-ray absorption being corrected through the correction processing; and (f) reconstructing the correction projection data to acquire correction CT image data.

As seen from the above, an object of the present invention is to provide a technology of properly specifying the metallic body position in a CT photographic region.

The above-described and other objects, features, aspects and advantages of the present invention will become more apparent from the following detailed description of the present invention when taken in conjunction with the accompanying drawings.

BRIEF DESCRIPTION OF THE DRAWING

FIG. 2 is a block diagram illustrating a schematic configuration of the X-ray CT photographic apparatus illustrated in FIG. 1;

FIG. 7 shows an example a binarized CT image in which the normal CT image is binarized;

FIG. 8 shows an example of a pseudo projection image expressed by pseudo CT image data;

FIG. 11 shows an example of a metal extraction projection image with respect to a metal equivalent region;

FIG. 12 shows an example of a correction projection image expressed by correction projection data;

DESCRIPTION OF THE PREFERRED EMBODIMENTS

Hereinafter, a preferred embodiment of the present invention will be described with reference to the accompanying drawings. In the accompanying drawings, for the sake convenience, sometimes the size or the number of pieces of each unit is magnified or simplified as needed.

1. Preferred Embodiment

Figure 1:
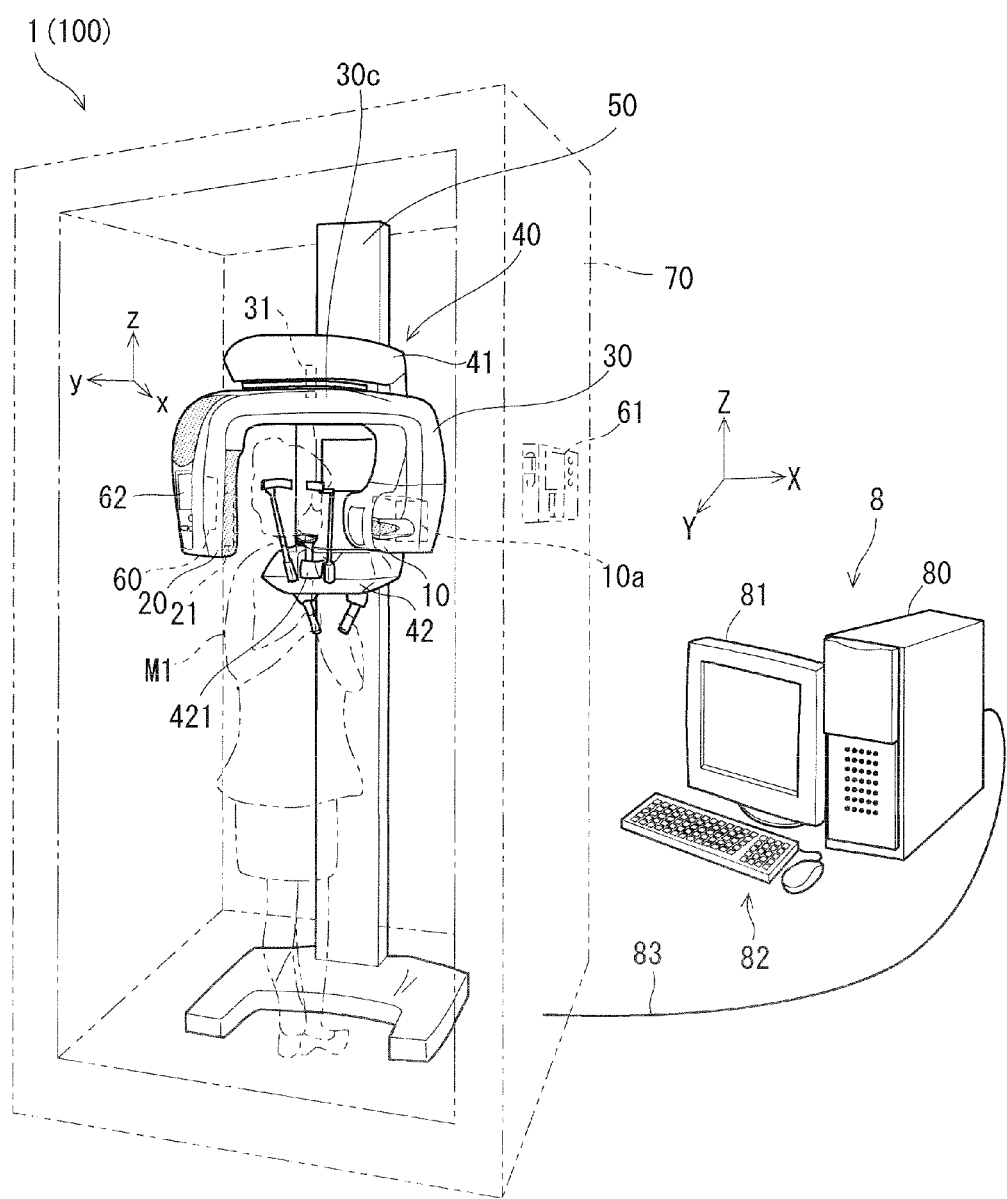
FIG. 1 is a schematic perspective view of an X-ray CT photographic apparatus according to a preferred embodiment of the present invention.
Figure 3:
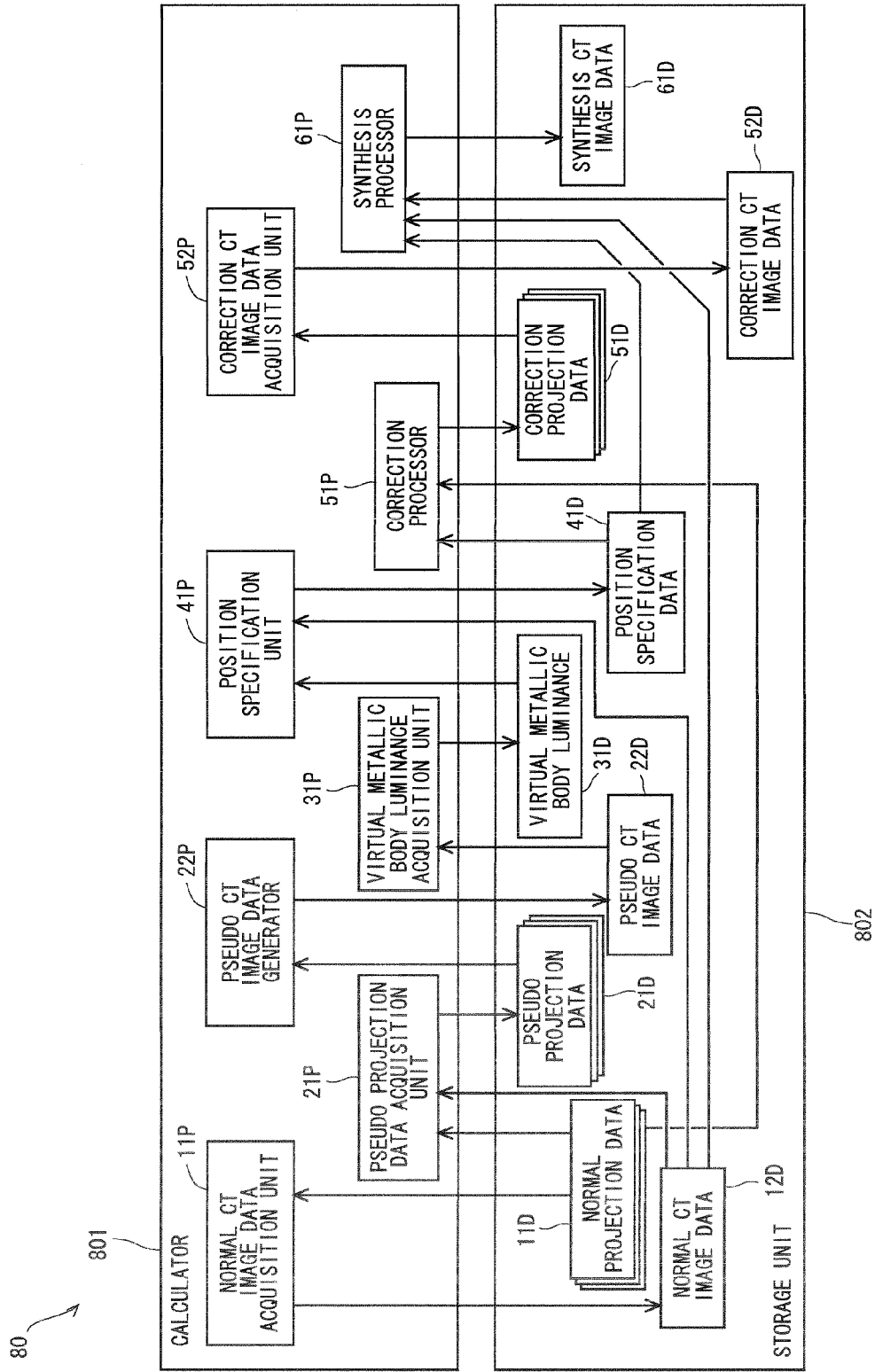
FIG. 3 is a view illustrating a functional block included in an image processing device illustrated in FIG. 1 together with a data flow.
Figure 4:
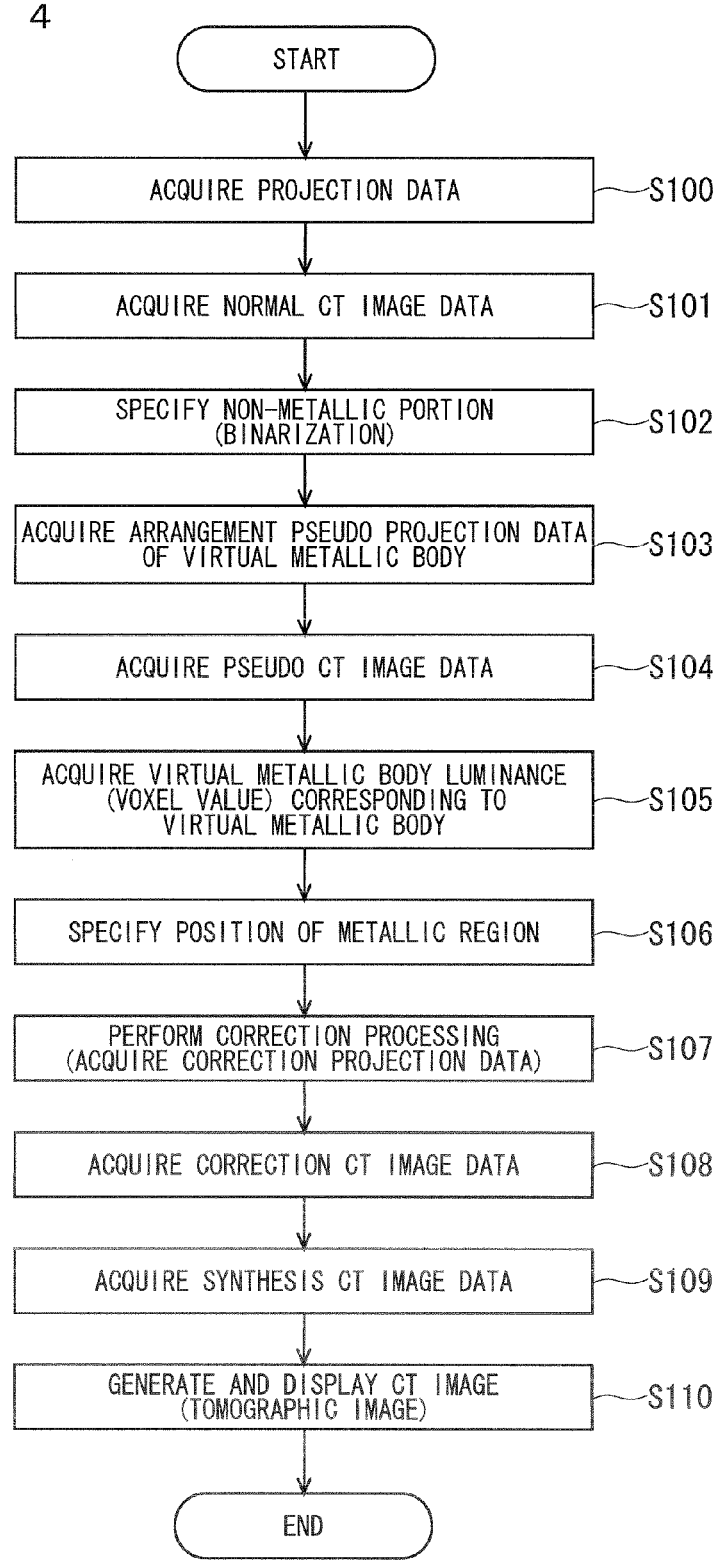
FIG. 4 is a flowchart of metallic artifact removal in the present invention.

FIG. 1 is a schematic perspective view of an X-ray CT photographic apparatus 1 according to a preferred embodiment of the present invention. FIG. 2 is a block diagram illustrating a schematic configuration of the X-ray CT photographic apparatus 1 illustrated in FIG. 1. FIG. 3 is a view illustrating a functional block included in an image processing device 80 illustrated in FIG. 1 together with a data flow. In addition, FIG. 4 is a flowchart of metallic artifact removal.

The X-ray CT photographic apparatus 1 illustrated in FIG. 1 is comprised of substantially three components: a manipulation display unit 61, a main body 2 (see FIG. 2), and an information processing device 8. The X-ray CT photographic apparatus 1 may be comprised of only an X-ray photographic apparatus main body 100, or may be comprised of X-ray photographic apparatus 100 and the information processing device 8. The information processing device 8 works as an individual information processing device, which does not always require the X-ray photographic apparatus main body 100. In this case, the information processing device 8 performs image processing as described in this specification as long as data of an X-ray image is inputted.

The manipulation display unit 61 sets a CT photographic region to an interest region, and also has a function of a display means, and the manipulation display unit 61 is a manipulation means that receives a manipulation of an operator. The main body 2 performs X-ray CT photography to the CT photographic region set by the manipulation display unit 61, and collects projection data. The information processing device 8 processes the projection data collected by the main body 2, and generates various images. In the field of X-ray photography, preferably, the main body 2 is accommodated in a hollow, vertically long, rectangular-solid-shaped X-ray protection chamber 70.

A main body controller 60 of the main body 2, a controller of the information processing device 8, and a calculator 801 perform the X-ray photography according to a program of the X-ray photography including the X-ray CT photography.

The main body 2, the manipulation display unit 61 mounted on a wall surface of the X-ray protection chamber 70, and the information processing device 8 disposed outside the X-ray protection chamber 70 are connected to one another using a connection cable 83.

The main body 2 includes an X-ray generation unit 10 and an X-ray detection unit 20. The X-ray generation unit 10 includes an X-ray generator 10a that emits an X-ray beam toward a subject M1, and the X-ray beam includes an X-ray cone beam BX configured by a bundle of X-rays. The X-ray detection unit 20 includes an X-ray detector 21, which detects the X-ray beam transmitted through the subject M1 after the X-ray generation unit 10 emits the X-ray beam. The main body 2 also includes a turning arm 30 that is a support body supporting the X-ray generation unit 10 and X-ray detection unit 20, a support post 50 that extends vertically, a lifting unit 40 that can vertically be lifted with respect to the support post 50 while suspending the turning arm 30, and the main body controller 60. The X-ray generation unit 10, the X-ray detection unit 20, and a beam shaping mechanism disposed on a side of the X-ray detection unit 20 with respect to the X-ray generation unit 10 constitute a photographic mechanism.

A MOS sensor, a CCD sensor, and a TFT can be cited as an example of the X-ray detector 21. Additionally, for example, a Flat Panel Detector (FPD) such as a CMOS sensor, an X-ray fluorescence intensifier tube (XII), other solid-state imaging elements and the like can be used as the X-ray detector 21.

The X-ray generation unit 10 and the X-ray detection unit 20 are suspended from and fixed to both end portions of a turning unit 30c of the turning arm 30, respectively. The X-ray generation unit 10 and the X-ray detection unit 20 are supported so as to be opposed to each other. The turning arm 30 is suspended from and fixed to the lifting unit 40 with a vertically extending turning shaft (not shown) interposed therebetween.

The turning arm 30 has a substantially inverted U-shape when viewed from the front side, and the turning arm 30 turns about the turning shaft 31 provided in an upper end portion thereof. In the preferred embodiment, the turning center is fixed to an upper frame 41. The X-ray generation unit 10 and the X-ray detection unit 20 are attached to the end portions of the turning arm 30, respectively.

The turning arm 30 of the preferred embodiment is formed into the U-shape. Alternatively, the turning arm 30 may be formed into another shape. For example, an annular member that is rotatably fitted in an outer circumferential portion of a columnar-shaped member with a ball bearing interposed therebetween may be used as the turning arm. In this case, the X-ray generation unit 10 and the X-ray detection unit 20 are attached to the annular member so as to be opposed to each other.

Hereinafter, a direction (in the preferred embodiment, a vertical direction namely, a longitudinal direction) parallel to an axis direction of the turning shaft 31 is referred to as a "Z-axis direction", a direction intersecting the Z-axis direction is referred to as an "X-axis direction", and a direction intersecting the X-axis direction and Z-axis direction is referred to as a "Y-axis direction". The X-axis direction and the Y-axis direction may arbitrarily be defined. However, in the preferred embodiment, when a test person who is of the subject M1 is positioned in the X-ray CT photographic apparatus 1 to face the support post 50 in correct position, a side-to-side direction of the test person is defines as the X-axis direction, and a front-back direction of the test person is defined as the Y-axis direction. In the preferred embodiment, it is assumed that the X-axis direction, the Y-axis direction, and the Z-axis direction are orthogonal to one another. Hereinafter, sometimes the Z-axis direction is referred to as the vertical direction, and a direction on a plane defined by a two-dimensional direction of the X-axis direction and Y-axis direction is referred to as a horizontal direction.

On the other hand, as to a three-dimensional coordinate on the turning arm 30, a direction in which the X-ray generation unit 10 and the X-ray detection unit 20 are opposed to each other is referred to as a "y-axis direction", a horizontal direction orthogonal to the y-axis direction is referred to as an "x-axis direction" and a vertical direction orthogonal to the x-axis direction and y-axis direction is referred to as a "z-axis direction". In the preferred embodiment and subsequent preferred embodiments, the z-axis direction and the Z-axis direction are parallel to each other. The turning arm 30 of the preferred embodiment turns with the turning shaft 31 extending in the vertical direction as a rotating axis. Accordingly, the xyz orthogonal coordinate system rotates about the Z-axis (=the z-axis) with respect to the XYZ orthogonal coordinate system.

When the X-ray generation unit 10 and X-ray detection unit 20 illustrated in FIG. 1 are viewed from above in plan, the direction from the X-ray generation unit 10 toward the X-ray detection unit 20 is referred to as a (+y) direction, a horizontal right-hand direction (in FIG. 1, a front side of the subject M1 in an orientation of the turning arm 30) orthogonal to the (+y) direction is referred to as a (+x) direction, and an upward direction of the vertical direction is referred to as a (+z) direction.

The lifting unit 40 includes the upper frame 41 (the support body retention unit) and a lower frame 42, and engages with the support post 50 that is vertically provided along the vertical direction. The turning shaft 31 is attached to the functioning upper frame 41. The lifting unit 40 moves in the vertical direction along the support post 50, whereby the turning arm 30 moves up and down.

As to the structure that turns the turning arm 30, the turning unit 30c of the turning arm 30 may be turnably provided to the turning shaft 31 which is unturnably fixed to the upper frame 41, and the turning arm 30 may turn with respect to the turning shaft 31. Alternatively, the turning unit 30c of the turning arm 30 may be unturnably fixed to the turning shaft 31 which is turnably provided to the upper frame 41, and the turning arm 30 may turn by turning the turning shaft 31.

The former structure described above is used in the example illustrated in FIG. 1. In this case, a turning motor (support body turning drive unit) is fixed to the inside of the turning arm 30, and a torque of the turning motor acts on the rotation of the turning arm 30, to which the turning motor is fixed, using a transmission mechanism (not illustrated) such as a belt and a pulley.

Alternatively, a turning motor (not illustrated) that turns the turning arm 30 about the turning shaft 31 may be provided in the upper frame 41, and the transmission mechanism (not illustrated), which includes a belt, a pulley, and a rotating shaft may transmit the torque of the turning motor (not illustrated) to the turning arm 30 to turn the turning arm 30 through the turning shaft 31.

Obviously, like the latter structure described above, a structure may be employed such that the turning unit 30c of the turning arm 30 is unturnably fixed to the turning shaft 31 which is turnably provided to the upper frame 41, and the turning arm 30 turns by turning the turning shaft 31. In this case, the turning motor is fixed to the inside of the upper frame 41, and the torque of the turning motor acts on the rotation of the turning shaft 31 using the transmission mechanism (not illustrated) such as a roller.

In the preferred embodiment, the turning shaft 31 is configured to extend along the vertical direction. Alternatively, the turning shaft 31 can be obliquely disposed with an arbitrary angle with respect to the vertical direction.

A bearing (not illustrated) is interposed between the turning shaft 31 and the turning arm 30. Therefore, the turning arm 30 can rotate smoothly with respect to the turning shaft 31. Herein, the turning shaft 31, the transmission mechanism that includes the bearing, the belt, the pulley, and the rotating shaft, and the turning motor make an example of the turning mechanism that turns the turning arm 30. In the preferred embodiment, the turning arm 30 turns with respect to the turning shaft 31 that is fixed to a fixed position so as not to rotate. However, as described above, the turning arm 30 may be turned by rotating the turning shaft 31 fixed to the turning arm 30 with respect to the upper frame 41. In this case, the bearing that rotatably supports the turning shaft 31 is formed on the side of the upper frame 41.

A subject retention unit 421 including an ear rod for fixing the subject M1 (in the preferred embodiment, the head of a human body) from both left and right sides and a chin rest for fixing the chin is provided in the lower frame 42.

The turning arm 30 is disposed in a pro per position by lifting and lowering the lifting unit 40 according to the height of the subject M1. At this point, the subject M1 is fixed to the subject retention unit 421. In the example illustrated in FIG. 1, the subject retention unit 421 retains the subject M1 such that the body axis of the subject M1 becomes substantially the same direction as the axis direction of the turning shaft 31.

The main body controller 60 is a controller that controls the operation of each configuration of the main body 2. For example, the main body controller 60 acts as an X-ray regulating controller and a drive controller. As illustrated in FIG. 1, the main body controller 60 is disposed inside the X-ray detection unit 20.

A manipulation display unit 62 is attached to a surface outside the main body controller 60, namely, on the side in the +Y direction of the X-ray detection unit 20. The manipulation display unit 62 is configured by buttons that are used to input various instructions and a touch panel that displays various pieces of information.

The manipulation display unit 61 is attached to a surface outside the X-ray protection chamber 70 that accommodates the main body 2 therein. The manipulation display unit 61 is connected to the main body controller 60, and configured by buttons and the like that are used to input various instructions and a touch panel that displays various pieces of information.

The operator (practitioner) may manipulate the main body 2 using the manipulation display unit 62, or manipulate the main body 2 using the manipulation display unit 61. The manipulation display unit 62 may differ from the manipulation display unit 61 in a manipulation content or a display content, or part or whole of the manipulation content or display content may be common to the manipulation display unit 62 and the manipulation display unit 61.

In the case that the X-ray protection chamber 70 is eliminated, the manipulation display unit 61 may be eliminated as well. One of the manipulation display unit 62 and the manipulation display unit 61 may be eliminated. The display and manipulation performed by the manipulation display unit 61 are described below. However, the display and manipulation performed by the manipulation display unit 61 may be replaced with the display and manipulation performed by the manipulation display unit 62.

The manipulation display unit 61 is also used to, for example, assign a position and the like of a photographic region of a biological organ and the like. There are various modes in the X-ray photography, and the mode can be selected by the manipulation of the manipulation display unit 61.

As illustrated in FIG. 3, a CPU included in the image processing device 80 operates according to a predetermined program, whereby the calculator 801 acts as a normal CT image data acquisition unit 11P, a pseudo projection data acquisition unit 21P, a pseudo CT image data generator 22P, a virtual metallic body luminance acquisition unit 31P, a position specification unit 41P, a correction processor 51P, a correction CT image data acquisition unit 52P, and a synthesis processor 61P.

A signal detected by each detection element of the X-ray detector 21 indicates intensity of the X-ray transmitted through the subject. The signal indicating the intensity of the transmission X-ray indicates the intensity of the X-ray transmitted through the subject. The signal indicating the intensity of the transmission X-ray is converted into a signal indicating an X-ray absorptance (or absorbance), whereby normal projection data 11D in FIG. 3 is generated and stored in a storage unit 802 (Step S100 in FIG. 4).

The normal CT image data acquisition unit 11P reconstructs (back projection) the normal projection data 11D to acquire normal CT image data 12D (Step S101 in FIG. 4). There is no particular limitation to reconstruction of calculation processing. For example, an FBP (Filtered Back Projection) method may be adopted. The generated normal CT image data 12D is three-dimensional volume data corresponding to a CT photographic region, and is configured by a voxel having a voxel value (luminance) corresponding to an X-ray absorption degree.

The pseudo projection data acquisition unit 21P arranges a virtual metallic body having a predetermined X-ray absorption coefficient in the photographic region of the X-ray CT photography in a pseudo manner. At this point, desirably, the virtual metallic body is arranged in the non-metallic region. Therefore, the pseudo projection data acquisition unit 21P binarizes the normal CT image data 12D using a predetermined threshold (Step S102 in FIG. 4). The threshold may be previously stored as an initial value in the storage unit 802 and the like, or automatically acquired by analyzing a histogram of the voxel value. Alternatively, the operator (practitioner) may assign the threshold. In each case, the metallic region and the non-metallic region are distinguished from each other by performing the binarization using the predetermined threshold. When distinguishing the metallic region and the non-metallic region from each other, the metallic region (a metallic body) existing currently in the CT photographic region is avoided to determine a place where the virtual metallic body is arranged. Accordingly, the threshold is not necessarily a value used to strictly distinguish the metallic region from the non-metallic region, but a value used to roughly distinguish the metallic region from the non-metallic region.

The configuration in which the metallic region is avoided to determine the place where the virtual metallic body is arranged through the processing in Step S102 may be eliminated, and instead the place where the virtual metallic body is arranged may be determined based on positional information on the subject M1, which is retained in the subject retention unit 421. In other words, sometimes the position of the metallic body of the subject M1 becomes roughly clear when the position of the subject M1 is determined. For example, in a dental clinic, because almost the metallic body is arranged in a position on a dental arch, the rough position of the metallic body can be relatively easily specified from the position of the subject M1. For example, even if a metallic body exists, the place where the metallic body exists can be determined on the dental arch. The positional overlapping of the metallic body and the virtual metallic body is avoided unless the virtual metallic body is arranged in the place corresponding to the dental arch of the head of a human body having a general skeletal frame. For example, as described later, a virtual metallic body may be arranged in positions of virtual metallic bodies 91VM and 93VM illustrated in FIG. 7. Obviously, the position where the virtual metallic body is arranged may be determined based on the positional information on the subject M1 and the positional information on the metallic body, which is obtained by the binarization processing.

The pseudo projection data acquisition unit 21P arranges the virtual metallic body in the non-metallic region in the pseudo manner, and acquires pseudo projection data 21D by calculation (Step S103 in FIG. 4). The X-ray absorption degree indicated by each pixel on the projection data is determined by an X-ray absorption factor of the transmitted substance. In other words, when an X-ray absorption coefficient $\mu$ of the virtual metallic body is well known, intensity I of the X-ray transmitted through the virtual metallic body is calculated based on the following equation.

$$I = I_0 \cdot \exp(-\mu \cdot T) \qquad \text{Equation (1)}$$

In the Equation (1), exp(x) represents the xth power of e (the base of natural logarithm, Napier number), $I_0$ represents original X-ray intensity (that is, an X-ray transmittance when the virtual metallic body is not arranged), and T represents a distance of the virtual metallic body transmitting the X-ray. $\mu$ is an X-ray attenuation coefficient of the virtual metallic body.

For example, a voxel size is set to 0.3 cubic millimeter, and the virtual metallic body is made of gold. In this case, the X-ray absorption coefficient (attenuation coefficient) $\mu$ is 0.97. The X-ray absorption coefficient $\mu$ is 0.94 in the case that the virtual metallic body is made of titanium. However, the X-ray absorption coefficient $\mu$ is properly set according to the state of the metal existing currently in the CT photographic region of the subject M1 or an environment in which the X-ray CT photography is performed.

Based on the Equation (1), the pseudo projection data acquisition unit 21P calculates a pixel value indicative of the new X-ray absorption degree in each pixel of the projection image expressed by the normal projection data 11D in the case that the virtual metallic body is arranged in the pseudo manner. Therefore, the pseudo projection data 21D is acquired.

The pseudo CT image data generator 22P reconstructs the pseudo projection data 21D to generate and acquire pseudo CT image data 22D (Step S104 in FIG. 4). This calculation processing is similar to the calculation processing performed by the normal CT image data acquisition unit 11P in Step S102.

The virtual metallic body luminance acquisition unit 31P acquires luminance (virtual metallic body luminance 31D) corresponding to the virtual metallic body in the pseudo CT image data 22D (Step S105 in FIG. 4). The virtual metallic body luminance 31D may include not one voxel value but plural voxel values. For example, the voxel values existing in a given range may be used as the virtual metallic body luminance 31D.

The position specification unit 41P specifies a metal equivalent region having the luminance corresponding to the virtual metallic body luminance 31D, for example, the position in the region where the absorption coefficient becomes identical to that of the virtual metallic body as the position (a metallic body position) in which the metallic body similar to the virtual metallic body exists (Step S106 in FIG. 4). Therefore, the position (the metallic body position) of the metallic body having the X-ray absorption coefficient similar to that of the virtual metallic body is specified. The position specification unit 41P retains the specified metallic body position as position specification data 41D in the storage unit 802. The position specification unit 41P may assign a range where the position of the metallic body equivalent region is specified. For example, in the case that the rough position of the metallic body is already known, a time necessary for the calculation processing can be shortened by restricting the range.

The correction processor 51P generates and acquires correction projection data 51D by performing correction processing of correcting degradation of the X-ray intensity due to X-ray absorption to the metallic body position specified by the position specification unit 41P in the normal projection data 11D (Step S107 in FIG. 4). Specifically, the correction processor 51P performs the correction processing to the luminance in the metallic body position in the projection image of the normal projection data 11D based on the luminance of each of the pixels on both sides in a predetermined direction. Preferably, linear interpolation in which the calculation is easily performed is adopted as a correction processing method. Alternatively, other interpolation processing techniques such as polynomial interpolation and wavelet interpolation or similar interpolation processing techniques may be adopted.

The correction CT image data acquisition unit 52P reconstructs the correction projection data 51D to generate and acquire correction CT image data 52D (Step S108 in FIG. 4). Therefore, the CT image data (volume data) in which the metallic body portion is corrected by the proper luminance is generated. The correction projection data 51D used at this time is data in which the metallic body is removed through the correction processing, and the removed metallic body is filled with a tissue having the same X-ray transmittance as the adjacent tissue, thereby hardly generating the artifact (however, for the metal having the relatively low X-ray absorption factor, sometimes special processing is performed like titanium as described later). Accordingly, the correction CT image data 52D is data in which a metallic artifact derived from the metallic body is reduced. In the case that the rough position of the metallic body is already known, the range where the correction projection data 51D is reconstructed may be restricted to a surrounding area of the metallic body, and the normal CT image data 12D may be directly used for the remaining portion of the CT photographic region. Therefore, a calculation processing time necessary to acquire the correction CT image data 52D can be shortened.

The synthesis processor 61P synthesizes the normal CT image data 12D and the correction CT image data 52D to generate and acquire synthesis CT image data 61D (Step S109 in FIG. 4). Particularly, the corrected luminance of the metal equivalent region in the correction CT image data 52D is converted into the luminance (that is, the original luminance equivalent to the metallic body) in the same position in the normal CT image data 12D. The position of the metal equivalent region is specified by the position specification unit 41P, so that the correct conversion can be performed. Therefore, the information on the luminance of the metallic body is buried in the correction CT image data 52D.

When the operator assigns a tomographic position through a manipulation unit 82, the image processing device 80 generates a tomographic image in the assigned position using the synthesis CT image data 61D, and displays the tomographic image on a display unit 81 (Step S110 in FIG. 4). The synthesis CT image data 61D is three-dimensional volume data, in which the luminance information on the metallic body is buried in the correction CT image data 52D in which the metallic body is removed to reduce the metallic artifact. Therefore, the CT image, in which the metallic body is photographed in the correct position while the metallic artifact is reduced, can be acquired using the synthesis image data 61D.

The flow of the metallic artifact removing processing is described above. A specific application example of the metallic artifact removing processing will be described below.

Figure 5:
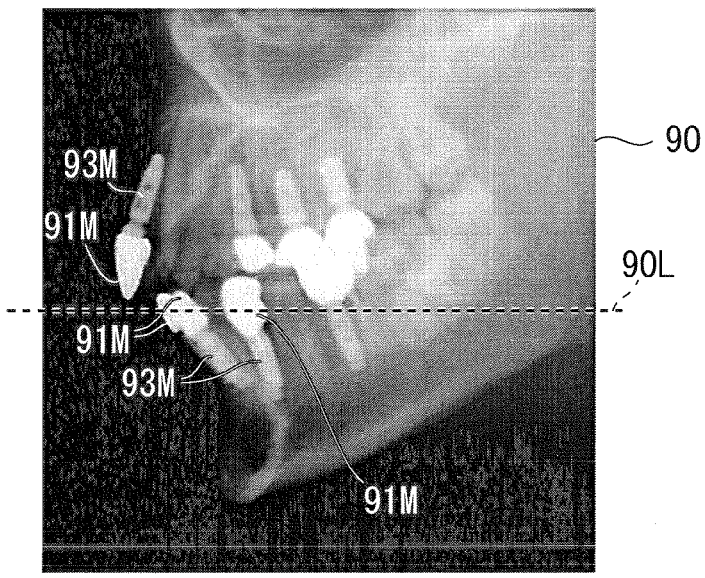
FIG. 5 shows an example of a normal projection image expressed by normal projection data.

FIG. 5 shows an example of a normal projection image 90 expressed by the normal projection data 11D. In the example shown in FIG. 5, plural gold materials 91M and plural titanium materials 93M, which are used as a dental prosthesis, are the metallic body in the CT photographic region. Specifically, the gold material 91M is used as an artificial tooth, and the titanium material 93M is used as an implant bolt used to attach artificial tooth to a chin.

The normal projection image 90 is expressed such that the luminance of the pixel becomes brighter with increasing X-ray absorption. Because the X-ray is absorbed in the gold material 91M and the titanium material 93M, the luminance becomes brighter in the gold material 91M and the titanium material 93M on the normal projection image 90.

Figure 6:
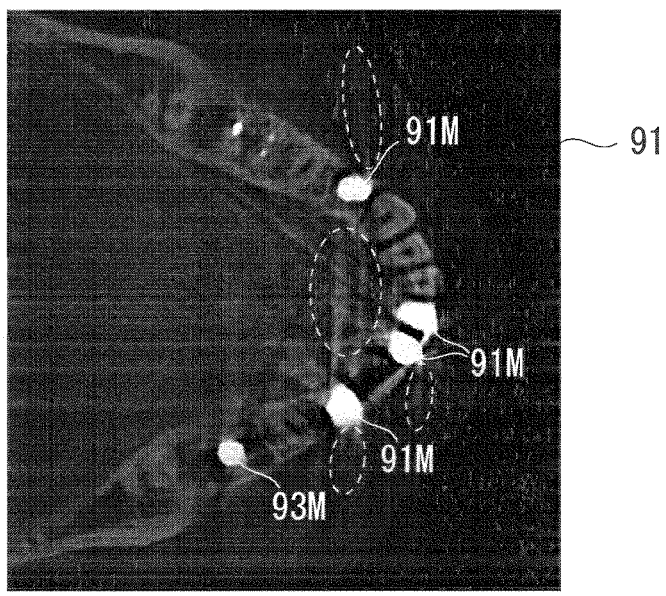
FIG. 6 shows an example of a normal CT image expressed by normal CT image data.

FIG. 6 shows an example of a normal CT image 91 expressed by the normal CT image data 12D. The normal CT image 91 shown in FIG. 6 is a tomographic image relating to the horizontal plane (an XY-plane) near the height of a lower jaw (specifically, the height of a line 90L illustrated in FIG. 5). As seen from FIG. 6, in the case that the normal reconstruction (for example, the FBP method) is performed, the streak noise (the metallic artifact) is generated in the surround (the region surrounded by a broken line) of the metallic body (in the preferred embodiment, the gold material 91M).

FIG. 7 shows an example of a binarized CT image 92 expressed by binarization CT image data in which the normal CT image 91 is binarized. As described above, the pseudo projection data acquisition unit 21P binarizes the normal CT image data 12D in order to determine the position where the virtual metallic body is arranged in the pseudo manner (S102 in FIG. 4). Therefore, the metallic body portion (the gold material 91M) and the non-metallic body portion are separated from each other by the binarization of the normal CT image 91. The pseudo projection data acquisition unit 21P arranges the virtual metallic body (in the preferred embodiment, the virtual gold material 91VM and the virtual titanium material 93VM) in the pseudo manner in the region (the non-metallic region) except the metal extracted in this manner. In the example shown in FIG. 7, the virtual metallic body is arranged so as to pierce a tongue portion inside the dental arch.

Each of the virtual gold material 91VM and the virtual titanium material 93VM is configured by a cylinder solid member extending in parallel with the turning shaft 31 of the turning arm 30 that is the support body of the X-ray CT photographic apparatus 1. A length in the z-axis direction of each of the virtual gold material 91VM and the virtual titanium material 93VM is set to be equal to or longer than a length in the z-axis direction of the CT photographic region expressed by the normal CT image data 12D.

FIG. 8 shows an example of a pseudo projection image 93 expressed by the pseudo projection data 21D. In the pseudo projection image 93, using the equation (1), the X-ray absorption degree is newly calculated in each pixel of the normal CT image 91 in the case that the virtual metallic body is arranged. In this situation, the X-ray absorption coefficient μ of the virtual gold material 91VM is set to 0.97, and the X-ray absorption coefficient μ of the virtual titanium material 93VM is set to 0.94. The pseudo projection image 93 in which the virtual gold material 91VM and the virtual titanium material 93VM are photographed in the pseudo manner is acquired by arranging the virtual gold material 91VM and the virtual titanium material 93VM in the CT photographic region in the pseudo manner. In FIG. 8, only the virtual gold material 91VM is seen because the virtual gold material 91VM is disposed on the front side. However, the virtual titanium material 93VM is also photographed in the pseudo projection image 93 when the pseudo projection image 93 is viewed from another angle.

As described above, the virtual gold material 91VM and the virtual titanium material 93VM are formed into the cylinder solid shape. Therefore, the X-ray absorption degree of the virtual metallic body is substantially homogenized among plural pseudo projection images 93 expressed by the pseudo projection data 21D. Because the appropriate virtual metallic body luminance 31D can be acquired, the position of the metallic body corresponding to the virtual metallic body can be successfully specified. However, the shape or size of the virtual metallic body can arbitrarily be changed. Preferably, the virtual metallic body is formed into the cylinder solid or the substantial cylinder solid.

Figure 9:
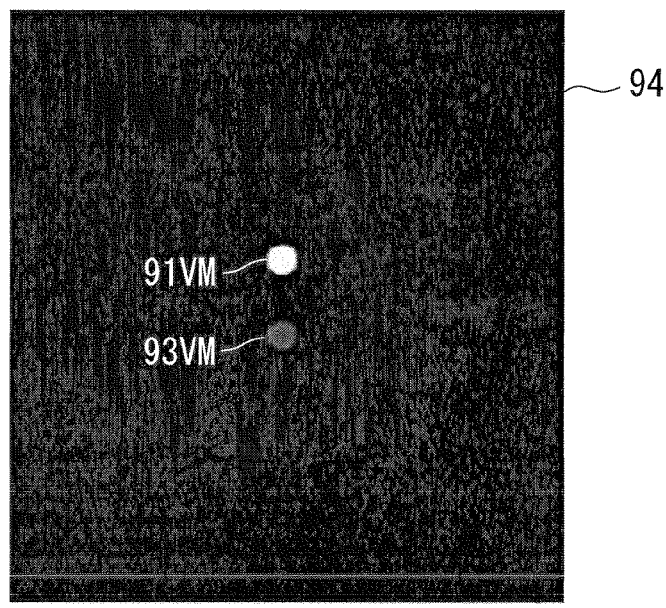
FIG. 9 shows an example of a pseudo CT image expressed by the pseudo CT image data.

FIG. 9 shows an example of a pseudo CT image 94 expressed by the pseudo CT image data 22D. As shown in FIG. 9, the pseudo CT image data 22D including the virtual metallic body is acquired by reconstructing the pseudo projection data 21D. Therefore, the luminance of each of the virtual gold material 91VM and the virtual titanium material 93VM is acquired on the pseudo CT image data 22 (Step S105 in FIG. 4). The luminance is acquired as the virtual metallic body luminance 31D. In FIG. 9, only the virtual gold material 91VM and the virtual titanium material 93VM are highlighted in order to emphasize the positions of the virtual gold material 91VM and virtual titanium material 93VM.

In the pseudo CT image data 22D, sometimes the virtual metallic body luminance 31D is not the luminance of one value but the luminance that is wide to some extent. For this reason, the luminance corresponding to each of the virtual gold material 91VM and the virtual titanium material 93VM is set to the luminance having a required range. In this situation, the luminance equivalent to the X-ray absorption coefficient μ of 0.97 or more is set to the luminance corresponding to the virtual gold material 91VM, and the luminance equivalent to the X-ray absorption coefficient μ that is greater than or equal to 0.94 and less than 0.97 is set to the luminance corresponding to the virtual titanium material 93VM.

The position specification unit 41P specifies the region having the luminance corresponding to the virtual metallic body luminance 31D as the metal equivalent region. Specifically, the gold equivalent region is specified as the metal equivalent region for the virtual gold material 91VM, and the titanium equivalent region is specified as the metal equivalent region for the virtual titanium material 93VM.

The CT image of the virtual metallic body portion and the CT image of the metallic body portion can be reconstructed under the same reconstruction condition by acquiring the pseudo projection data 21D. For example, even if the condition varies such that the subjects have different bone densities, the accuracy of the specification of the metal equivalent region can be enhanced.

Figure 10:
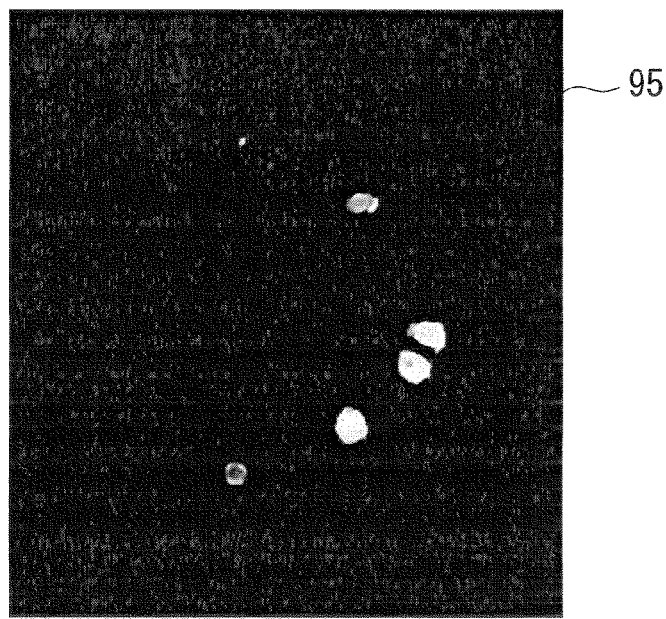
FIG. 10 shows an example of a region separation CT image that is separated into a gold equivalent region (white), a titanium equivalent region (gray), and a non-metal equivalent region (black)

FIG. 10 shows an example of a region separation CT image 95 that is separated into a gold equivalent region (white), a titanium equivalent region (gray), and a non-metal equivalent region (black). Specifically, the gold equivalent region means the region having the luminance (at this point, the X-ray absorption coefficient μ of 0.97 or more) corresponding to the luminance of the virtual gold material 91VM in the normal CT image data 12D, the titanium equivalent region means the region having the luminance (the X-ray absorption coefficient μ is greater than or equal to 0.94 and less than 0.97) corresponding to the luminance of the virtual titanium material 93VM in the normal CT image data 12D, and the non-metal equivalent region means the region (the region where X-ray absorption coefficient μ is less than 0.94) that does not correspond to the gold equivalent region and the titanium equivalent region in the normal CT image data 12D. More specifically, the CT image data (region separation CT image data) expressing the region separation CT image 95 is generated by quantifying the normal CT image data 12D to three levels with the virtual metallic body luminance 31D relating to the virtual gold material 91VM and virtual titanium material 93VM as the threshold. The region separation CT image 95 may be generated by binarizing the normal CT image data 12D. For example, the region where the X-ray absorption coefficient μ is greater than 0.94 may be set to the metal equivalent region. The position of metal equivalent region can be specified by applying the virtual metallic body luminance 31D to the normal CT image data 12D, besides, it can be specified by applying the virtual metallic body luminance 31D to the pseudo CT image data 22D. In this case, calculation adjustment by, for example, subtruction and the like that is done for obstructing the position of the virtual metallic body itself should be regarded as the position of the metal equivalent region.

When acquiring the region separation CT image data expressing the region separation CT image 95, the position specification unit 41P performs the calculation processing of projecting the region separation CT image data onto the two-dimensional plane. As a result, the gold equivalent region, the titanium equivalent region, and the non-metal equivalent region can be distinguished from one another on the projection image expressed by the two-dimensional plane. Thus, the position specification unit 41P specifies the positions of gold and titanium that are the metallic body, and acquires the positional information as the position specification data 41D.

FIG. 11 shows an example of a metal extraction projection image 96 with respect to the metal equivalent region. The metal extraction projection image 96 shown in FIG. 11 is the projection image that is obtained on the assumption that, in the normal CT image data 12D, the metal equivalent region indicated by the region separation CT image data is irradiated with the X-ray from the same direction (in this case, the left side of the subject M1) as the X-ray CT photography, and the metal extraction projection image 96 is the image acquired through the predetermined calculation processing. In FIG. 11, the region (a the background) except the metal equivalent region is shown in gray for the sake of convenience. As seen from the metal extraction projection image 96, in the gold equivalent region, the luminance is saturated because the X-ray is substantially absorbed. On the other hand, it is found that in the titanium equivalent region, the portion having the high luminance and the portion having the low luminance exist because the X-ray is partially transmitted. The metal extraction projection image 96 is used in the following correction processing.

FIG. 12 shows an example of a correction projection image 97 expressed by correction projection data 51D. The correction projection image 97 is acquired such that the correction processor 51P refers to the position specification data 41D to perform the correction processing to the metallic body portion included in the normal projection data 11D. As seen from the correction projection image 97, in the preferred embodiment, the different pieces of correction processing are performed to the gold equivalent region and the titanium equivalent region, respectively. The correction processing will be described below.

Figure 13:
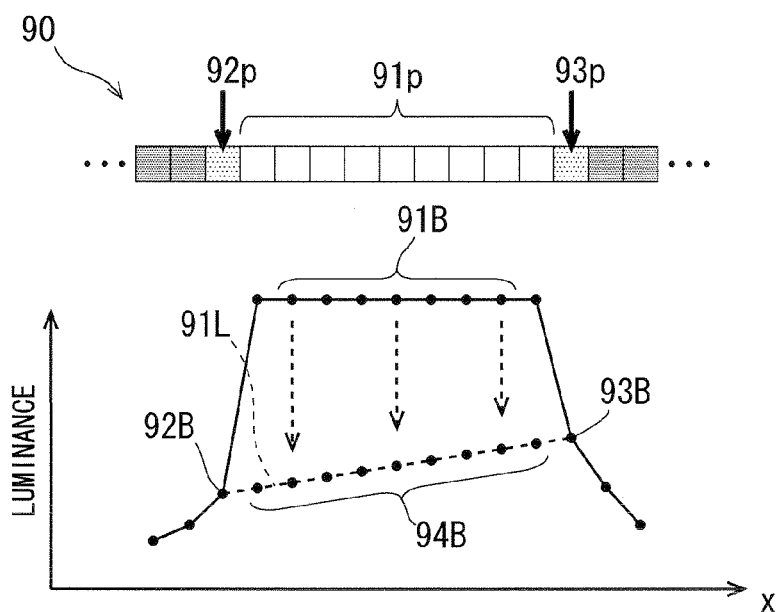
FIG. 13 shows interpolation processing performed to the gold equivalent region by a correction processor.

FIG. 13 shows interpolation processing performed to the gold equivalent region by the correction processor 51P. In FIG. 13, plural successive pixels 91p specified as the gold equivalent region in the inside portion of plural pixels arrayed in the horizontal direction (the x-axis direction) and pixels (such as pixels 92p and 93p) located on both sides of the plural pixels 91p are shown in the normal projection image 90 (for example, see FIG. 5) expressed by the normal projection data 11D. The luminance of each pixel group is plotted on a two-dimensional graph illustrated in a lower stage of FIG. 13. As can be seen from the line graph connecting the plotted points, because the pixel 91p constituting the gold equivalent region has the X-ray absorption degree larger than that of the surround, the pixel 91p has luminance 91B higher than that of the surround.

In the case that the correction processor 51P performs the interpolation processing to the sequence of pixels 91p, the correction processor 51P extracts the surrounding area of the sequence of pixels 91p equivalent to the gold equivalent region in the x-axis direction, for example, the pixels 92p and 93p adjacent to the sequence of pixels 91p. The correction processor 51P determines new luminance 94B in each successive pixels 91p by performing the interpolation using pieces of luminance 92B and 93B of the pixels 92p and 93p. For example, in the case that linear interpolation (straight-line interpolation) is performed, the luminance 92B of the pixel 92p and the luminance 93B of the pixel 93p are connected by the line segment 91L indicated by broken line in FIG. 13. The luminance in the corresponding position on the line segment 91L is used as the new luminance 94B of the pixel 91p in each sequence of pixels 91p.

In the example illustrated in FIG. 13, the interpolation processing is performed in the horizontal direction of the normal projection image 90. Alternatively, the interpolation processing may be performed in the perpendicular direction of the normal projection image 90. In other words, the interpolation processing may be performed using the luminance of the pixel adjacent to the metal equivalent region in the perpendicular direction. The pixels on the left and right sides in the horizontal direction or the pixels on the top and bottom sides in the perpendicular direction may be used as the surrounding pixels used in the interpolation. The pixels on the left, right, top, and bottom sides may be used as well.

On the normal projection image 90 of FIG. 13, possibly, the luminance of the pixel (for example, the pixels 92p and 93p) corresponding to the surround of the gold material 91M includes the noise, because the gold material 91M has the extremely high X-ray absorption degree. Therefore, the gold equivalent region specified by the position specification unit 41P may be enlarged (thickened) in the horizontal direction or perpendicular direction of the image by at least one adjacent pixel or more, specifically one pixel or two pixels. The correction processor 51P may perform the interpolation processing with the enlarged region as the new gold equivalent region. In the interpolation processing, the use of the luminance of the pixel (for example, the pixels 92p and 93p) that possibly includes the noise can be restricted.

As described above, in the gold equivalent region, the interpolation processing of the luminance is performed using the luminance of the pixel equivalent to the boundary portion of the region outside the gold equivalent region, whereby the gold equivalent region is removed from the original normal projection image 90. On the other hand, the correction processing of removing the X-ray absorption degree of the titanium material 93 from the titanium equivalent region in the original normal projection image 90 is performed in the titanium equivalent region. Specifically, the calculation processing of subtracting the luminance (that is, the luminance of the pixel in the corresponding position on the metal extraction projection image 96) equivalent to the X-ray absorption amount generated by the transmission of the titanium material 93M is performed to each pixel in the titanium equivalent region of the normal projection image 90 as illustrated in FIG. 5. Therefore, the projection image in which the X-ray absorption degree equivalent to the titanium material 93M is removed can be acquired from the normal projection image 90.

For the metal, such as titanium, which has the relatively low X-ray absorption factor, the transmission of the X-ray is relatively generated compared with the metal, such as gold, which has the high X-ray absorption factor. For this reason, the X-ray absorption degree indicated by the pixel in the position where the X-ray is transmitted through the titanium material 93M on the normal projection image 90 includes information (the tooth and living tissues such as a muscular tissue) except the titanium portion transmitting the X-ray. Accordingly, in the titanium equivalent region, the information on the X-ray absorption degree except titanium is left by subtracting the luminance, and the information on the CT photographic region of the subject M1 can be retained while lost through the correction processing as little as possible. Like the gold equivalent region, the correction processing such as the linear interpolation described in FIG. 13 may be applied to the titanium equivalent region.

Figure 14:
FIG. 14 shows an example of a correction CT image expressed by correction CT image data.

Because the titanium material 93M has the X-ray absorption factor lower than that of the gold material 91M, the metallic artifact is hardly generated in the reconstruction. Therefore, the correction processing may not be performed. However, rapid attenuation is generated in the case that the transmission distance of the X-ray through the titanium material 93M is lengthened such that the plural titanium materials 93M exist on a traveling path of the X-ray. Therefore, when the projection data is reconstructed, possibly, the metallic artifact is generated due to the titanium material 93M. Accordingly, in order to obtain the good CT image, preferably the correction processing is performed to the metallic material such as the titanium equivalent region having a relatively low X-ray absorption factor such that X-ray absorption degree derived from the metal is removed from the normal projection data 11D FIG. 14 shows an example of a correction CT image 98 expressed by the correction CT image data 52D. As shown in FIG. 14, the correction CT image 98 in which the gold material 91M and titanium material 93M photographed in the normal CT image 91 (see FIG. 6) are partially or wholly removed is generated through the correction processing. As seen from FIG. 14, in the correction CT image 98, the metallic artifact, which is generated in the surrounding area of the metallic body and surrounded by the broken line in FIG. 14, is reduced by removing the metallic body.

Figure 15:
FIG. 15 shows an example of a synthesis CT image expressed by synthesis CT image data.

FIG. 15 shows an example of a synthesis CT image 99 expressed by the synthesis CT image data 61D. As described above, the synthesis CT image data 61D (see FIG. 3) is the volume data that is obtained by converting the luminance (the voxel value) of the metal equivalent region (the gold equivalent region and the titanium equivalent region) in the correction CT image data 52D into the luminance in the same position in the normal CT image data 12D. Through this conversion processing, the information on the metallic body is added to the synthesis CT image data 61D in which the metallic body is removed. Therefore, like the synthesis CT image 99 shown in FIG. 15, the image of the metallic body is synthesized on the correction CT image 98 in which the metallic body is removed. Thus, according to the synthesis CT image data 61D, the CT image expressing the original CT photographic region in which the metallic artifact is reduced can be generated.

The correction processor 51P may perform low-pass filter processing in order to enhance the accuracy of the image reconstruction. Generally, in the case that the X-ray image is detected by the X-ray detector 21 including a detection surface configured by many pixels, a boundary between the metallic region and the non-metallic region is used as an edge, and an image signal of the projection image in an edge portion becomes a high-frequency component when the image of the edge is clear. In this situation, in calculating the CT reconstruction, sometimes the edge portion has an influence on the reconstruction image by an aliasing effect. Therefore, the influence may be reduced by applying a low-pass filter only to the edge portion.

According to the configuration which performs Step S106, the position specification unit 41P can specify the metallic body position with high accuracy. Therefore, the position corresponding to the boundary between the metal equivalent region and the region except the metal equivalent region in the normal projection data received by the detection surface of the X-ray detector 21, namely, the position of the edge can also be specified with high accuracy. With this, the low-pass filter is applied only to the position of the detected edge to suppress the aliasing, and the accuracy of the image reconstruction can be improved.

In addition, the X-ray CT photographic apparatus 1 may perform local X-ray CT photography. The local X-ray CT photography means photography in which only a partial region in the subject M1, namely, a local portion, is irradiated with the X-ray to detect the transmitted X-ray and the CT image is reconstructed, or photography in which a region including the local portion is irradiated with the X-ray to detect only the X-ray transmitted through the local portion and the CT image is reconstructed. For example, a diagnosis whether a wisdom tooth is in an overturned state in a buries wisdom tooth region, a diagnosis whether various tumors are widened, or a diagnosis of part of the dental arch or a surrounding portion (a tongue side portion or a cheek portion) of the dental arch is occasionally made in the dental clinic. In such cases, for example, a local CT photographic region is set for a couple of teeth as a local photographic object. In the projection image acquired by the local X-ray CT photography, because of the small X-ray bundle, scattering line generation amount is decreased compared with the photography of the large region, and the small-noise CT image can be reconstructed.

Hence the pseudo manner is executed in simulation manner, the words having been described above can be converted as follows: the pseudo manner can be converted to simulation manner; the pseudo projection data can be converted to simulated projection data; the pseudo projection data acquisition unit can be converted to simulated projection data acquisition unit; the pseudo projection image can be converted to simulated projection image; the pseudo CT image data can be converted to simulated CT image data; the pseudo CT image data generator can be converted to simulated CT image data generator; the virtual metallic body can be converted to simulated metallic body; the virtual titanium material can be converted to simulated titanium material; the virtual gold material can be converted to simulated gold material; and the virtual metallic body luminance can be converted to simulated metallic body luminance.

2. Modification

Although the preferred embodiment is described above, the present invention is not limited to the preferred embodiment, but various modifications can be made.

For example, in the preferred embodiment, the virtual gold material 91VM and the virtual titanium material 93VM are arranged in the pseudo manner as the virtual metallic body. Alternatively, another virtual metal may be arranged. Only one kind of virtual metallic body or at least three kinds of virtual metallic bodies may be arranged.

Each configuration of the preferred embodiment and modification can properly be combined as long as the configurations are consistent with each other.

While the invention has been shown and described in detail, the foregoing description is in all aspects illustrative and not restrictive. It should be, therefore, understood that numerous modifications and variations can be devised without departing from the scope of the invention.

What is claimed is:

1. An image processing device for acquiring CT image data by reconstructing projection data which is acquired by performing X-ray CT photography of a region including a metallic body in a subject, the image processing device comprising:

a pseudo projection data acquisition unit that acquires pseudo projection data by calculation when a virtual metallic body having a predetermined X-ray absorption coefficient is set in a photographic region of said X-ray CT photography in a pseudo manner based on said projection data;

a pseudo CT image data generator that reconstructs said pseudo projection data to generate pseudo CT image data;

a virtual metallic body luminance acquisition unit that acquires virtual metallic body luminance that is luminance corresponding to said virtual metallic body in said pseudo CT image data;

a position specification unit that specifies a position of a metal equivalent region having luminance corresponding to said virtual metallic body luminance in CT image data or in the pseudo CT image data;

a correction processor that acquires correction projection data by performing correction processing to the luminance of said metal equivalent region in said projection data, degradation of X-ray intensity due to X-ray absorption being corrected through the correction processing; and a correction CT image data acquisition unit that reconstructs said correction projection data to acquire correction CT image data.

2. The image processing device according to claim 1, wherein said correction processor performs said correction processing to the luminance of said metal equivalent region in said projection data according to luminance in a surrounding area of the metal equivalent region.

3. The image processing device according to claim 1, further comprising a synthesis processor that synthesizes said correction CT image data and said CT image data by converting the luminance of said metal equivalent region in said correction CT image data according to luminance in an identical position in said CT image data.

4. The image processing device according to claim 3, wherein
said pseudo projection data acquisition unit acquires said pseudo projection data by calculation when the a plurality of kinds of virtual metallic bodies having said X-ray absorption coefficients different from each other are arranged in a pseudo manner based on said projection data, and
said position specification unit individually specifies a position of a region having luminance corresponding to said virtual metallic body luminance of each of said plurality of kinds of virtual metallic bodies in said CT image data, in which said projection data is reconstructed, as said metal equivalent region.

5. The image processing device according to claim 4, wherein said correction processor corrects said luminance by subtracting an X-ray absorption degree of said metal equivalent region corresponding to the virtual metallic body from X-ray absorption degrees of said metal equivalent regions equivalent to some virtual metallic bodies having lower X-ray absorption coefficients in said plurality of kinds of virtual metallic bodies in said projection data.

6. The image processing device according to claim 5, wherein said position specification unit distinguishes a metallic body region corresponding to higher X-ray absorption coefficient in said two kinds of said virtual metallic bodies, a metallic body region corresponding to lower X-ray absorption coefficient, and a region not corresponding to said two kinds of virtual metallic bodies from one another by quantifying said CT image data to three levels with luminance corresponding to luminance of each of said two kinds of virtual metallic bodies as a threshold.

7. The image processing device according to claim 4, wherein said position specification unit distinguishes a metallic body region corresponding to higher X-ray absorption coefficient in said two kinds of said virtual metallic bodies, a metallic body region corresponding to lower X-ray absorption coefficient, and a region not corresponding to said two kinds of virtual metallic bodies from one another by quantifying said CT image data to three levels with luminance corresponding to luminance of each of said two kinds of virtual metallic bodies as a threshold.

8. The image processing device according to claim 1, wherein said projection data is acquired by local X-ray CT photography in which only a partial region in subject is irradiated with an X-ray.

9. The image processing device according to claim 1, wherein said projection data is acquired by an X-ray CT photographic apparatus,
the X-ray CT photographic apparatus comprising:
an X-ray generator that generates the X-ray;
an X-ray detector that detects said X-ray transmitted through the subject;
a support body that supports said X-ray generator and said X-ray detector while said X-ray generator and said X-ray detector are opposed to each other in relation to said subject; and
a support body turning drive unit that turns said support body about a turning shaft to turn said X-ray generator and said X-ray detector about said subject, and
said virtual metallic body being formed into a cylinder solid or a substantial cylinder solid, the cylinder solid or the substantial cylinder solid being arranged so as to extend in parallel with said turning shaft.

10. The image processing device according to claim 9, wherein
said X-ray CT photographic apparatus further comprises a subject retention unit that retains the subject, and
said virtual metallic body is arranged in a pseudo manner in a position different from said metallic body, which is determined based on positional information on said subject, the positional information on said subject being retained in said subject retention unit.

11. The image processing device according to claim 1, wherein
said position specification unit distinguishes the metal equivalent region that is equivalent to said virtual metallic body from a region that is not equivalent to said virtual metallic body by binarizing said CT image data with luminance corresponding to the luminance of said virtual metallic body as a threshold.

12. The image processing device according to claim 1, wherein said correction processor sets a region where said metal equivalent region in said projection data is enlarged so as to include at least one adjacent pixel to a target region of said correction processing.

13. The image processing device according to claim 1, wherein said correction processor performs low-pass filter processing to projection data in a boundary portion between said metal equivalent region and a region except the metal equivalent region in said projection data.

14. An X-ray CT photographic apparatus for acquiring CT image data by reconstructing projection data acquired by performing X-ray CT photography of a region including a metallic body in a subject, the X-ray CT photographic apparatus comprising:
a pseudo projection data acquisition unit that acquires pseudo projection data by calculation when a virtual metallic body having a predetermined X-ray absorption coefficient is arranged in a photographic region of said X-ray CT photography in a pseudo manner based on said projection data;
a pseudo CT image data generator that reconstructs said pseudo projection data to generate pseudo CT image data;
a virtual metallic body luminance acquisition unit that acquires virtual metallic body luminance that is luminance corresponding to said virtual metallic body in said pseudo CT image data;
a position specification unit that specifies a position of a metal equivalent region having luminance corresponding to said virtual metallic body luminance in CT image data or in the pseudo CT image data;

a correction processor that acquires correction projection data by performing correction processing to the luminance of said metal equivalent region in said projection data, degradation of X-ray intensity due to X-ray absorption being corrected through the correction processing; and a correction CT image data acquisition unit that reconstructs said correction projection data to acquire correction CT image data.

15. An image processing method of acquiring CT image data by reconstructing projection data acquired by performing X-ray CT photography of a region including a metallic body in a subject, the image processing method comprising the steps of:

(a) acquiring pseudo projection data by calculation when a virtual metallic body having a predetermined X-ray absorption coefficient is arranged in a photographic region of said X-ray CT photography in a pseudo manner based on said projection data;

(b) reconstructing said pseudo projection data to generate pseudo CT image data;

(c) acquiring virtual metallic body luminance of said virtual metallic body in said pseudo CT image data;

(d) specifying a position of a metal equivalent region having luminance corresponding to said virtual metallic body luminance in the CT image data or in the pseudo CT image data;

(e) acquiring correction projection data by performing correction processing to the luminance of said metal equivalent region in said projection data, degradation of X-ray intensity due to X-ray absorption being corrected through the correction processing; and (f) reconstructing said correction projection data to acquire correction CT image data.

\* \* \* \* \*